US008187854B2

(12) United States Patent
Vind et al.

(10) Patent No.: US 8,187,854 B2
(45) Date of Patent: May 29, 2012

(54) LIPASE VARIANTS

(75) Inventors: Jesper Vind, Vaerloese (DK); Jürgen Carsten Franz Knötzel, Copenhagen O (DK); Kim Borch, Birkeroed (DK); Allan Svendsen, Horsholm (DK); Thomas Honger Callisen, Frederiksberg (DK); Debbie Yaver, Davis, CA (US); Mads Eskelund Bjornvad, Virum (DK); Peter Kamp Hansen, Lejre (DK); Haiyan Ge, Davis, CA (US); Michael Lamsa, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 313 days.

(21) Appl. No.: 12/161,582

(22) PCT Filed: Jan. 22, 2007

(86) PCT No.: PCT/US2007/060841
§ 371 (c)(1),
(2), (4) Date: Sep. 3, 2008

(87) PCT Pub. No.: WO2007/087508
PCT Pub. Date: Aug. 2, 2007

(65) Prior Publication Data
US 2009/0029440 A1   Jan. 29, 2009

Related U.S. Application Data

(60) Provisional application No. 60/761,109, filed on Jan. 23, 2006, provisional application No. 60/854,891, filed on Oct. 27, 2006.

(51) Int. Cl.
*C12N 9/20* (2006.01)
*C12N 1/20* (2006.01)
*C12N 15/00* (2006.01)
*C07H 21/04* (2006.01)

(52) U.S. Cl. ............... 435/198; 435/252.3; 435/320.1; 536/23.2

(58) Field of Classification Search .............. 435/198, 435/252.3, 320.1; 536/23.2
See application file for complete search history.

(56) References Cited

U.S. PATENT DOCUMENTS

| 5,892,013 | A | 4/1999 | Svendsen et al. |
| 6,624,129 | B1 | 9/2003 | Borch et al. |
| 6,939,702 | B1 * | 9/2005 | Vind et al. ............ 435/198 |
| 7,786,067 | B2 * | 8/2010 | Souter et al. ............ 510/419 |
| 7,790,666 | B2 * | 9/2010 | Souter et al. ............ 510/419 |

FOREIGN PATENT DOCUMENTS

| EP | 258068 | 3/1988 |
| EP | 305216 | 3/1989 |
| EP | 430315 | 6/1991 |
| WO | 92/05249 A1 | 4/1995 |
| WO | WO 97/04079 | 2/1997 |
| WO | WO 97/07202 | 2/1997 |
| WO | WO 00/32758 | 6/2000 |
| WO | WO 00/60063 | 10/2000 |
| WO | 01/83770 A2 | 11/2001 |
| WO | 02/055679 A2 | 7/2002 |
| WO | WO 02/062973 | 8/2002 |

* cited by examiner

*Primary Examiner* — Tekchand Saidha
(74) *Attorney, Agent, or Firm* — Kristin J. McNamara

(57) ABSTRACT

The invention provides variant lipases, preferably, variants with reduced tendency to odor generation obtained by introducing mutations in one or more regions identified in a parent lipase.

18 Claims, 3 Drawing Sheets

```
ID NO 1:    SSSSTQDYRIASEAEIKAHTFYTALSANA
ID NO 2:     SSSTQDYRIASEAEIKAHTFYTALSANA
ID NO 3:     SIDGGIRAATSQEINELTYYTTLSANS
ID NO 4:    SASDGGKVVAATTAQIQEFTKYAGIAATA
ID NO 5:        TAGHALAASTQ GISEDLYSRL VEMATISQAA
ID NO 6:        TAGHALAASTQ GISEDLYSRL VEMATISQAA
ID NO 7:             AVGVTTTDFSNFKFYIQHGAAA
ID NO 8:              TVTTQDLSNFRPYLQHADAA
ID NO 9:              DIPTTQLEDFKFVQYAAAT
ID NO 10:             DVSTSELDQFEFWVQYAAAS
ID NO 11:             SVSTSTLDELQLFAQWSAAA
ID NO 12:             SVSTSTLDELQLFSQWSAAA
ID NO 13:             DVSSSLLNNLDLFAQYSAAA
ID NO 14:             EVSQDLFNQFNLFAQYSAAA
ID NO 15:           PQDAYTASHADLVKYATYAGLA

ID NO 1:   YCRTVIPG      GRWSCPHCGVAS  NLQITKTPST  LITDTNVLVAV
ID NO 2:   YCRTVIPG      GQWSCPHCDVAP  NLNITKTPTT  LITDTNVLVAV
ID NO 3:   YCRTVIPG      ATWDCIHCDATE  DLKIIKTWST  LIYDTNAMVAR
ID NO 4:   YCRSVVPG      NKWDCVQCQKWVP DGKIITTFTS  LLSDTNGYVLR
ID NO 5:   YADLCNIPST                  IIKGEKIYNSQTDINGWILR
ID NO 6:   YADLCNIPST                  IIKGEKIYNSQTDINGWILR
ID NO 7:   YC  NSEAAA  GSKITCSNNGCPTVQGNGATIVTSF  VGSKTGIGGYVAT
ID NO 8:   YC  NFNTAV  GKPVHCSAGNCPDIEKDAAIVVGSV  VGTKTGIGAYVAT
ID NO 9:   YCPNNYVAKD  GEKLNCSVGNCPDVEAAGSTVKLSFS DDTITDTAGFVAV
ID NO 10:  YYEADYTAQV  GDKLSCSKGNCPEVEATGATVSYDFS DSTITDTAGYIAV
ID NO 11:  YCSNNID SK  DSNLTCTANACPSVEEASTTMLLEFDLTNDFGGTAGFLAA
ID NO 12:  YCSNNID SD  DSNVTCTADACPSVEEASTKMLLEFDLTNNFGGTAGFLAA
ID NO 13:  YCDENLN ST  GTKLTCSVGNCPLVEAASTQSLDRFNESSSYGNPAGYLAA
ID NO 14:  YCGKNNDAPA  GTNITCTGNACPEVEKADATFLYSFE DSGVGDVTGFLAL
ID NO 15:  YQTTDAWPAS                 RTVPKDTTLISSFD  HTLKGSSGYIAF

ID NO 1:   GEKEKTIYVV FRGTSSIRNA IADIVFVPVN YPPV  NGA KVHKGFLDSY
ID NO 2:   GENEKTIYVV FRGTSSIRNA IADIVFVPVN YPPV  NGA KVHKGFLDSY
ID NO 3:   GDSEKTIYIV FRGSSSIRNW IADLTFVPVS YPPV  SGT KVHKGFLDSY
ID NO 4:   SDKQKTIYLV FRGTNSFESA ITDIVFNFSD YKPV  KGA KVHAGFLSSY
ID NO 5:   DDSSKEIITV FRGTGSDTNL QLDTNYTLTP FDTLPQCNGC EVHGGYYIGW
ID NO 6:   DDSSKEITTV FRGTGSDTNL QLDTNYTLTP FDTLPQCNSC EVHGGYYIGW
ID NO 7:   DSARKEIVVS FRGSINIRNW LTNLDFG QE  DCSL  VSGC GVHSGFQRAW
ID NO 8:   DNARKEIVVS VRGSINVRNW ITNFNFG QK  TCDL  VAGC GVHTGFLDAW
ID NO 9:   DNTNKAIVVA FRGSYSIRNW VTDATFP QT  DPGL  CDGC KAELGFWTAW
ID NO 10:  DHTNSAVVLA FRGSYSVRNW VADATFV HT  NFGL  CDGC LAELGFWSSW
ID NO 11:  DNTNKRLVVA FRGSSTIENW IANLDFILED NDDL  CTGC KVHTGFWKAW
ID NO 12:  DNTNKRLVVA FRGSSTIKNW IADLDFILQD NDDL  CTGC KVHTGFWKAW
ID NO 13:  DETNKLLVLS FRGSADIANW VANLNFGLED ASDL  CSGC EVHSGFWKAW
ID NO 14:  DNTNKLIVLS FRGSRSIENW IGNLNFDLKE INDI  CSGC RGHDGFTSSW
ID NO 15:  NEPCKEIIVA YRGTDSLIDW LTNLNFDKTA WEAN  ISNS LVHEGFLNAY

ID NO 1:   NEVQDKLVAE VKAQLDRHPG YKIVVTGHSL GGATAVLSALDLYHHGHA
ID NO 2:   NEVQDKLVAE VKAQLDRHPG YKIVVTGHSL GGATAVLSALDLYHHGHD
ID NO 3:   GEVQNELVAT VLDQFKQYPS YKVAVTGHSL GGATALLCALDLYQREEGLS
ID NO 4:   EQVVNDYFPV VQEQLTAHPT YKVIVTGHSL GGAQALLAGMDLYQREPRLS
ID NO 5:   VSVQDQVESL VKQQVSQYPD YALTVTGHSL GASLAALTAAQL SATYD
ID NO 6:   ISVQDQVESL VQQQVSQFPD YALTVTGHSL GASLAALTAAQL SATYD
ID NO 7:   NEISSQATAA VASARKANPS FNVISTGHSL GGAVAVLAAANLRVGGT
ID NO 8:   EKVAANVKAA VSAAKTANPT FKFVVTGHSL GGAVATIAAAYLRKDGF
ID NO 9:   KVVRDKIIKT LDELKFEHSD YKIVVVGHSL GAAIASLAAADLRTKNY
ID NO 10:  KLVRDDIIKE LKEVVAQNPN YELVVVGHSL GAAVATLAATDLRGKGYP
ID NO 11:  ESAADELTSK IKSAMSTYSG YTLYFTGHSL GGALATGATVLRNDGY
ID NO 12:  EAAADNLTSK IKSAMSTYSG YTLYFTGHSL GGALATGATVLRNDGY
ID NO 13:  SEIADTITSK VESALSDHSD YSLVLTGHSY GAALAALAATALRNSGH
```

Figure 1 (cont.)

```
ID NO 14:  RSVADTLRQK VEDAVREHPD YRVVFTGHSL GGALATVAGADLRGNGY
ID NO 15:  LVSMQQVQEA VDSLLAKCPD ATISFTGHSL GGALACISMVDTAQRHRGI

ID NO 1:   NIEIYTQG  QPRIGTPAFA NYVIGT      KIPYQRLVHERDIVPHL
ID NO 2:   NIEIYTQG  QPRIGTPEFA NYVIGT      KIPYQRLVNERDIVPHL
ID NO 3:   SSNLFLYTQG QPRVGDPAFA NYVVST     GIPYRRTVNERDIVPHL
ID NO 4:   PKNLSIFTVG GPRVGNPTFA YYVEST     GIPFQRTVHKRDIVPHV
ID NO 5:   NIRLYTFG  EPRSGNQAFA SYMNDAFQASSPDTTQYFRVTHANDGIPNL
ID NO 6:   NIRLYTFG  EPRS NQAFA SYMNDAFQASSPDTTQYFRVTHANDGIPNL
ID NO 7:   PVDIYTYG  SPRVGNAQLS AFVSNQ     AGGEYRVTHADDPVPRL
ID NO 8:   PFDLYTYG  SPRVGNDFFA NFVTQQ     TGAEYRVTHGDDPVPRL
ID NO 9:   DAILYAYA  APRVANKPLA EFITNQ     GNNYRFTHNDDPVPKL
ID NO 10:  SAKLYAYA  SPRVGNAALA KYITAQ     GNNFRFTHTNDPVPKL
ID NO 11:  SVELYTYG  CPRIGNYALA EHITSQ     GSGANFRVTHLNDIVPRV
ID NO 12:  SVELYTYG  CPRVGNYALA EHITSQ     GSGANFPVTHLNDIVPRV
ID NO 13:  SVELYNYG  QPRLGNEALA TYITDQ     NKGGNYRVTHTNDIVPKL
ID NO 14:  DIDVFSYG  APRVGNRAFA EFLTVQ     TGGTLYRITHTNDIVPRL
ID NO 15:  KMQMFTYG  QPRTGNQAFA EYVENL     GHPVFRVVYRHDIVPRM

ID NO 1:   PPGAFGFLHA GEEFWIMK      DSSLRVCPNGIETDNCSNSIV
ID NO 2:   PPGAFGFLHA GEEFWIMK      DSSLRVCPNGIETDNCSNSIV
ID NO 3:   PPAAFGFLHA GEEYWITD      NSPETVQVCTSDLETSDCSNSIV
ID NO 4:   PPQSFGFLHP GVESWIKS      GTSNVQICTSEIETKDCSNSIV
ID NO 5:   PPVEQGYAHG GVEYWSV       DPYSAQNTFVCTGDEVQCCE AQGGQG
ID NO 6:   PPADEGYAHG VVEYWSV       DPYSAQNTFVCTGDEVQCCE AQGGQG
ID NO 7:   PPLIFGYRHT TPEFWLSGGGGDKVDYTISDVKVCEGAANLG CNGGTL
ID NO 8:   PPIVFGYRHT SPEYWLNG GPLDKDYTVTEIKVCEGIANVM CNGGTI
ID NO 9:   PLLTMGYVHI SPEYYITA PDNTTVTDNQVTVLDGYVNFK GNTGTS
ID NO 10:  PLLSMGYVHV SPEYWITS PNNATVSTSDIKVIDGDVSPD GNTGTG
ID NO 11:  PPMDFGFSQP SPEYWITS GNGASVTASDIEVIEGINSTA GNAGEA
ID NO 12:  PPMDFGFSQP SPEYWITS GTGASVTASDIELIEGINSTA GNAGEA
ID NO 13:  PPTLLGYHHF SPEYYISS ADEATVTTTDVTEVTGIDATG GNDGTD
ID NO 14:  PPREFGYSHS SPEYWIKS GTLVPVTRNDIVKIEGIDATG GNNQPN
ID NO 15:  PPMDLGFQHH GQEVWYEG       DENIKFCKGEGENLTCELGVP

ID NO 1:   PFT SVIDHLSYLDMNTGL CL
ID NO 2:   PFT SVIDHLSYLDMNTGL CL
ID NO 3:   PFT SVLDHLSYFGINTGL CT
ID NO 4:   PFT SILDHLSYFDINEGS CL
ID NO 5:   VN      NAHTTYF GMTSGACTW
ID NO 6:   VN      NAHTTYF GMTSGHCTW
ID NO 7:   GL      DIAAHLHYF QATDA CNAGGFSWR R
ID NO 8:   GL      DILAHITYF QSMAT CAPIAIPWK R
ID NO 9:   GGLPDLLAFHSHVWYF IHADACKGPGLPLR
ID NO 10:  LPLLTDFEAHIWYF VQVDA GKGPGLPFK R
ID NO 11:  TV      SVLAHLWYF FAISE CLL
ID NO 12:  TV      DVLAHLWYF FAISE CLL
ID NO 13:  GT      SIDAHRWYF IYISE CS
ID NO 14:  IP      DIPAHLWYF GLIGT CL
ID NO 15:  FSEL NAKDHSEYP GMH
```

| ID NO: | Micro organism | SEQ ID NO.: |
| --- | --- | --- |
| 1. | *Absidia reflexa* | 3 |
| 2. | *Absidia corymbifera* | 4 |
| 3. | *Rhizmucor miehei* | 5 |
| 4. | *Rhizopus delemar (oryzea)* | 6 |
| 5. | *Aspergillus niger* | 7 |
| 6. | *Aspergillus tubingensis* | 8 |
| 7. | *Fusarium oxysporum* | 9 |
| 8. | *Fusarium heterosporum* | 10 |
| 9. | *Aspergillus oryzae* | 11 |
| 10. | *Penicilium camembertii* | 12 |

Figure 1 (cont.)

| | | |
|---|---|---|
| 11. | *Aspergillus foetidus* | 13 |
| 12 | *Aspergillus niger* | 14 |
| 13. | *Aspergillus oryzea* | 15 |
| 14. | *Thermomyces lanuginosus* | 2 |
| 15. | *Landerina penisapora* | 16 |

Figure 1. Alignment of lipase sequences.

SEQUENCE LISTING

<160> NUMBER OF SEQ ID NOS: 18

<210> SEQ ID NO 1
<211> LENGTH: 807
<212> TYPE: DNA
<213> ORGANISM: Thermomyces lanuginosus
<220> FEATURE:
<221> NAME/KEY: CDS
<222> LOCATION: (1)..(807)
<220> FEATURE:
<221> NAME/KEY: mat_peptide
<222> LOCATION: (1)..()

<400> SEQUENCE: 1

-continued

| | |
|---|---|
| gag gtc tcg cag gat ctg ttt aac cag ttc aat ctc ttt gca cag tat<br>Glu Val Ser Gln Asp Leu Phe Asn Gln Phe Asn Leu Phe Ala Gln Tyr<br>1                    5                    10                 15 | 48 |
| tct gca gcc gca tac tgc gga aaa aac aat gat gcc cca gct ggt aca<br>Ser Ala Ala Ala Tyr Cys Gly Lys Asn Asn Asp Ala Pro Ala Gly Thr<br>                  20                   25                   30 | 96 |
| aac att acg tgc acg gga aat gcc tgc ccc gag gta gag aag gcg gat<br>Asn Ile Thr Cys Thr Gly Asn Ala Cys Pro Glu Val Glu Lys Ala Asp<br>                35                   40                  45 | 144 |
| gca acg ttt ctc tac tcg ttt gaa gac tct gga gtg ggc gat gtc acc<br>Ala Thr Phe Leu Tyr Ser Phe Glu Asp Ser Gly Val Gly Asp Val Thr<br>        50                    55                   60 | 192 |
| ggc ttc ctt gct ctc gac aac acg aac aaa ttg atc gtc ctc tct ttc<br>Gly Phe Leu Ala Leu Asp Asn Thr Asn Lys Leu Ile Val Leu Ser Phe<br>65                    70                   75                 80 | 240 |
| cgt ggc tct cgt tcc ata gag aac tgg atc ggg aat ctt aac ttc gac<br>Arg Gly Ser Arg Ser Ile Glu Asn Trp Ile Gly Asn Leu Asn Phe Asp<br>                        85                   90               95 | 288 |
| ttg aaa gaa ata aat gac att tgc tcc ggc tgc agg gga cat gac ggc<br>Leu Lys Glu Ile Asn Asp Ile Cys Ser Gly Cys Arg Gly His Asp Gly<br>                  100                105               110 | 336 |
| ttc act tcg tcc tgg agg tct gta gcc gat acg tta agg cag aag gtg<br>Phe Thr Ser Ser Trp Arg Ser Val Ala Asp Thr Leu Arg Gln Lys Val<br>             115                120               125 | 384 |
| gag gat gct gtg agg gag cat ccc gac tat cgc gtg gtg ttt acc gga<br>Glu Asp Ala Val Arg Glu His Pro Asp Tyr Arg Val Val Phe Thr Gly<br>130                   135                140 | 432 |
| cat agc ttg ggt ggt gca ttg gca act gtt gcc gga gca gac ctg cgt<br>His Ser Leu Gly Gly Ala Leu Ala Thr Val Ala Gly Ala Asp Leu Arg<br>145                   150                155               160 | 480 |
| gga aat ggg tat gat atc gac gtg ttt tca tat ggc gcc ccc cga gtc<br>Gly Asn Gly Tyr Asp Ile Asp Val Phe Ser Tyr Gly Ala Pro Arg Val<br>                  165                170               175 | 528 |
| gga aac agg gct ttt gca gaa ttc ctg acc gta cag acc ggc gga aca<br>Gly Asn Arg Ala Phe Ala Glu Phe Leu Thr Val Gln Thr Gly Gly Thr<br>                    180                185               190 | 576 |
| ctc tac cgc att acc cac acc aat gat att gtc cct aga ctc ccg ccg<br>Leu Tyr Arg Ile Thr His Thr Asn Asp Ile Val Pro Arg Leu Pro Pro<br>             195                200               205 | 624 |
| cgc gaa ttc ggt tac agc cat tct agc cca gag tac tgg atc aaa tct<br>Arg Glu Phe Gly Tyr Ser His Ser Ser Pro Glu Tyr Trp Ile Lys Ser<br>                210                215               220 | 672 |
| gga acc ctt gtc ccc gtc acc cga aac gat atc gtg aag ata gaa ggc<br>Gly Thr Leu Val Pro Val Thr Arg Asn Asp Ile Val Lys Ile Glu Gly<br>225                   230                235               240 | 720 |
| atc gat gcc acc ggc ggc aat aac cag cct aac att ccg gat atc cct<br>Ile Asp Ala Thr Gly Gly Asn Asn Gln Pro Asn Ile Pro Asp Ile Pro<br>                    245                250               255 | 768 |
| gcg cac cta tgg tac ttc ggg tta att ggg aca tgt ctt<br>Ala His Leu Trp Tyr Phe Gly Leu Ile Gly Thr Cys Leu<br>             260                265 | 807 |

```
<210> SEQ ID NO 2
<211> LENGTH: 269
<212> TYPE: PRT
<213> ORGANISM: Thermomyces lanuginosus

<400> SEQUENCE: 2
```

Glu Val Ser Gln Asp Leu Phe Asn Gln Phe Asn Leu Phe Ala Gln Tyr
1                   5                   10                15

Ser Ala Ala Ala Tyr Cys Gly Lys Asn Asn Asp Ala Pro Ala Gly Thr

```
                    20                  25                  30
Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
 50                  55                  60

Gly Phe Leu Ala Leu Asp Asn Thr Asn Lys Leu Ile Val Leu Ser Phe
 65                  70                  75                  80

Arg Gly Ser Arg Ser Ile Glu Asn Trp Ile Gly Asn Leu Asn Phe Asp
                    85                  90                  95

Leu Lys Glu Ile Asn Asp Ile Cys Ser Gly Cys Arg Gly His Asp Gly
                100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
        130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 3
<211> LENGTH: 265
<212> TYPE: PRT
<213> ORGANISM: Absidia reflexa

<400> SEQUENCE: 3

Ser Ser Ser Ser Thr Gln Asp Tyr Arg Ile Ala Ser Glu Ala Glu Ile
 1               5                  10                  15

Lys Ala His Thr Phe Tyr Thr Ala Leu Ser Ala Asn Ala Tyr Cys Arg
                20                  25                  30

Thr Val Ile Pro Gly Gly Arg Trp Ser Cys Pro His Cys Gly Val Ala
            35                  40                  45

Ser Asn Leu Gln Ile Thr Lys Thr Phe Ser Thr Leu Ile Thr Asp Thr
 50                  55                  60

Asn Val Leu Val Ala Val Gly Glu Lys Glu Lys Thr Ile Tyr Val Val
 65                  70                  75                  80

Phe Arg Gly Thr Ser Ser Ile Arg Asn Ala Ile Ala Asp Ile Val Phe
                85                  90                  95

Val Pro Val Asn Tyr Pro Pro Asn Gly Ala Lys Val His Lys Gly
                100                 105                 110

Phe Leu Asp Ser Tyr Asn Glu Val Gln Asp Lys Leu Val Ala Glu Val
            115                 120                 125

Lys Ala Gln Leu Asp Arg His Pro Gly Tyr Lys Ile Val Val Thr Gly
```

```
                     130                 135                 140
His Ser Leu Gly Gly Ala Thr Ala Val Leu Ser Ala Leu Asp Leu Tyr
145                 150                 155                 160

His His Gly His Ala Asn Ile Glu Ile Tyr Thr Gln Gly Gln Pro Arg
                    165                 170                 175

Ile Gly Thr Pro Ala Phe Ala Asn Tyr Val Ile Gly Thr Lys Ile Pro
                180                 185                 190

Tyr Gln Arg Leu Val His Glu Arg Asp Ile Val Pro His Leu Pro Pro
            195                 200                 205

Gly Ala Phe Gly Phe Leu His Ala Gly Glu Glu Phe Trp Ile Met Lys
        210                 215                 220

Asp Ser Ser Leu Arg Val Cys Pro Asn Gly Ile Glu Thr Asp Asn Cys
225                 230                 235                 240

Ser Asn Ser Ile Val Pro Phe Thr Ser Val Ile Asp His Leu Ser Tyr
                    245                 250                 255

Leu Asp Met Asn Thr Gly Leu Cys Leu
                260                 265

<210> SEQ ID NO 4
<211> LENGTH: 264
<212> TYPE: PRT
<213> ORGANISM: Absidia corymbifera

<400> SEQUENCE: 4

Ser Ser Ser Thr Gln Asp Tyr Arg Ile Ala Ser Glu Ala Glu Ile Lys
1               5                   10                  15

Ala His Thr Phe Tyr Thr Ala Leu Ser Ala Asn Ala Tyr Cys Arg Thr
                20                  25                  30

Val Ile Pro Gly Gly Gln Trp Ser Cys Pro His Cys Asp Val Ala Pro
                35                  40                  45

Asn Leu Asn Ile Thr Lys Thr Phe Thr Thr Leu Ile Thr Asp Thr Asn
50                  55                  60

Val Leu Val Ala Val Gly Glu Asn Glu Lys Thr Ile Tyr Val Val Phe
65                  70                  75                  80

Arg Gly Thr Ser Ser Ile Arg Asn Ala Ile Ala Asp Ile Val Phe Val
                85                  90                  95

Pro Val Asn Tyr Pro Pro Val Asn Gly Ala Lys Val His Lys Gly Phe
                100                 105                 110

Leu Asp Ser Tyr Asn Glu Val Gln Asp Lys Leu Val Ala Glu Val Lys
            115                 120                 125

Ala Gln Leu Asp Arg His Pro Gly Tyr Lys Ile Val Val Thr Gly His
        130                 135                 140

Ser Leu Gly Gly Ala Thr Ala Val Leu Ser Ala Leu Asp Leu Tyr His
145                 150                 155                 160

His Gly His Asp Asn Ile Glu Ile Tyr Thr Gln Gly Gln Pro Arg Ile
                    165                 170                 175

Gly Thr Pro Glu Phe Ala Asn Tyr Val Ile Gly Thr Lys Ile Pro Tyr
                180                 185                 190

Gln Arg Leu Val Asn Glu Arg Asp Ile Val Pro His Leu Pro Pro Gly
            195                 200                 205

Ala Phe Gly Phe Leu His Ala Gly Glu Glu Phe Trp Ile Met Lys Asp
        210                 215                 220

Ser Ser Leu Arg Val Cys Pro Asn Gly Ile Glu Thr Asp Asn Cys Ser
225                 230                 235                 240

Asn Ser Ile Val Pro Phe Thr Ser Val Ile Asp His Leu Ser Tyr Leu
```

Asp Met Asn Thr Gly Leu Cys Leu
                260

<210> SEQ ID NO 5
<211> LENGTH: 269
<212> TYPE: PRT
<213> ORGANISM: Rhizomucor miehei

<400> SEQUENCE: 5

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
            20                  25                  30

Ile Pro Gly Ala Thr Trp Asp Cys Ile His Cys Asp Ala Thr Glu Asp
        35                  40                  45

Leu Lys Ile Ile Lys Thr Trp Ser Thr Leu Ile Tyr Asp Thr Asn Ala
    50                  55                  60

Met Val Ala Arg Gly Asp Ser Glu Lys Thr Ile Tyr Ile Val Phe Arg
65                  70                  75                  80

Gly Ser Ser Ser Ile Arg Asn Trp Ile Ala Asp Leu Thr Phe Val Pro
                85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
    130                 135                 140

Leu Gly Gly Ala Thr Ala Leu Leu Cys Ala Leu Asp Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
    210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
            260                 265

<210> SEQ ID NO 6
<211> LENGTH: 271
<212> TYPE: PRT
<213> ORGANISM: Rhizopus oryzae

<400> SEQUENCE: 6

Ser Ala Ser Asp Gly Gly Lys Val Val Ala Ala Thr Thr Ala Gln Ile
1               5                   10                  15

Gln Glu Phe Thr Lys Tyr Ala Gly Ile Ala Ala Thr Ala Tyr Cys Arg
            20                  25                  30

Ser Val Val Pro Gly Asn Lys Trp Asp Cys Val Gln Cys Gln Lys Trp
        35                  40                  45

```
Val Pro Asp Gly Lys Ile Ile Thr Thr Phe Thr Ser Leu Leu Ser Asp
     50                  55                  60

Thr Asn Gly Tyr Val Leu Arg Ser Asp Lys Gln Lys Thr Ile Tyr Leu
 65                  70                  75                  80

Val Phe Arg Gly Thr Asn Ser Phe Arg Ser Ala Ile Thr Asp Ile Val
                 85                  90                  95

Phe Asn Phe Ser Asp Tyr Lys Pro Val Lys Gly Ala Lys Val His Ala
                100                 105                 110

Gly Phe Leu Ser Ser Tyr Glu Gln Val Val Asn Asp Tyr Phe Pro Val
            115                 120                 125

Val Gln Glu Gln Leu Thr Ala His Pro Thr Tyr Lys Val Ile Val Thr
130                 135                 140

Gly His Ser Leu Gly Gly Ala Gln Ala Leu Leu Ala Gly Met Asp Leu
145                 150                 155                 160

Tyr Gln Arg Glu Pro Arg Leu Ser Pro Lys Asn Leu Ser Ile Phe Thr
                165                 170                 175

Val Gly Gly Pro Arg Val Gly Asn Pro Thr Phe Ala Tyr Tyr Val Glu
            180                 185                 190

Ser Thr Gly Ile Pro Phe Gln Arg Thr Val His Lys Arg Asp Ile Val
        195                 200                 205

Pro His Val Pro Pro Gln Ser Phe Gly Phe Leu His Pro Gly Val Glu
210                 215                 220

Ser Trp Ile Lys Ser Gly Thr Ser Asn Val Gln Ile Cys Thr Ser Glu
225                 230                 235                 240

Ile Glu Thr Lys Asp Cys Ser Asn Ser Ile Val Pro Phe Thr Ser Ile
                245                 250                 255

Leu Asp His Leu Ser Tyr Phe Asp Ile Asn Glu Gly Ser Cys Leu
            260                 265                 270

<210> SEQ ID NO 7
<211> LENGTH: 267
<212> TYPE: PRT
<213> ORGANISM: Aspergillus niger

<400> SEQUENCE: 7

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
        35                  40                  45

Tyr Asn Ser Gln Thr Asp Ile Asn Gly Trp Ile Leu Arg Asp Asp Ser
 50                  55                  60

Ser Lys Glu Ile Ile Thr Val Phe Arg Gly Thr Gly Ser Asp Thr Asn
 65                  70                  75                  80

Leu Gln Leu Asp Thr Asn Tyr Thr Leu Thr Pro Phe Asp Thr Leu Pro
                85                  90                  95

Gln Cys Asn Gly Cys Glu Val His Gly Gly Tyr Ile Gly Trp Val
            100                 105                 110

Ser Val Gln Asp Gln Val Glu Ser Leu Val Lys Gln Val Ser Gln
            115                 120                 125

Tyr Pro Asp Tyr Ala Leu Thr Val Thr Gly His Ser Leu Gly Ala Ser
130                 135                 140

Leu Ala Ala Leu Thr Ala Ala Gln Leu Ser Ala Thr Tyr Asp Asn Ile
145                 150                 155                 160
```

```
Arg Leu Tyr Thr Phe Gly Glu Pro Arg Ser Gly Asn Gln Ala Phe Ala
                165                 170                 175

Ser Tyr Met Asn Asp Ala Phe Gln Ala Ser Ser Pro Asp Thr Thr Gln
            180                 185                 190

Tyr Phe Arg Val Thr His Ala Asn Asp Gly Ile Pro Asn Leu Pro Pro
        195                 200                 205

Val Glu Gln Gly Tyr Ala His Gly Gly Val Glu Tyr Trp Ser Val Asp
    210                 215                 220

Pro Tyr Ser Ala Gln Asn Thr Phe Val Cys Thr Gly Asp Glu Val Gln
225                 230                 235                 240

Cys Cys Glu Ala Gln Gly Gly Gln Gly Val Asn Asn Ala His Thr Thr
                245                 250                 255

Tyr Phe Gly Met Thr Ser Gly Ala Cys Thr Trp
                260                 265

<210> SEQ ID NO 8
<211> LENGTH: 266
<212> TYPE: PRT
<213> ORGANISM: Aspergillus tubingensis

<400> SEQUENCE: 8

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
        35                  40                  45

Tyr Asn Ser Gln Thr Asp Ile Asn Gly Trp Ile Leu Arg Asp Asp Ser
    50                  55                  60

Ser Lys Glu Ile Ile Thr Val Phe Arg Gly Thr Gly Ser Asp Thr Asn
65                  70                  75                  80

Leu Gln Leu Asp Thr Asn Tyr Thr Leu Thr Pro Phe Asp Thr Leu Pro
                85                  90                  95

Gln Cys Asn Ser Cys Glu Val His Gly Gly Tyr Tyr Ile Gly Trp Ile
            100                 105                 110

Ser Val Gln Asp Gln Val Glu Ser Leu Val Gln Gln Val Ser Gln
        115                 120                 125

Phe Pro Asp Tyr Ala Leu Thr Val Thr Gly His Ser Leu Gly Ala Ser
130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Asn Gln Ala Phe Ala Ser
                165                 170                 175

Tyr Met Asn Asp Ala Phe Gln Ala Ser Ser Pro Asp Thr Thr Gln Tyr
            180                 185                 190

Phe Arg Val Thr His Ala Asn Asp Gly Ile Pro Asn Leu Pro Pro Ala
        195                 200                 205

Asp Glu Gly Tyr Ala His Gly Val Val Glu Tyr Trp Ser Val Asp Pro
    210                 215                 220

Tyr Ser Ala Gln Asn Thr Phe Val Cys Thr Gly Asp Glu Val Gln Cys
225                 230                 235                 240

Cys Glu Ala Gln Gly Gly Gln Gly Val Asn Asn Ala His Thr Thr Tyr
                245                 250                 255

Phe Gly Met Thr Ser Gly His Cys Thr Trp
                260                 265
```

<210> SEQ ID NO 9
<211> LENGTH: 276
<212> TYPE: PRT
<213> ORGANISM: Fusarium oxysporum

<400> SEQUENCE: 9

```
Ala Val Gly Val Thr Thr Thr Asp Phe Ser Asn Phe Lys Phe Tyr Ile
1               5                   10                  15

Gln His Gly Ala Ala Ala Tyr Cys Asn Ser Glu Ala Ala Ala Gly Ser
            20                  25                  30

Lys Ile Thr Cys Ser Asn Asn Gly Cys Pro Thr Val Gln Gly Asn Gly
        35                  40                  45

Ala Thr Ile Val Thr Ser Phe Val Gly Ser Lys Thr Gly Ile Gly Gly
    50                  55                  60

Tyr Val Ala Thr Asp Ser Ala Arg Lys Glu Ile Val Val Ser Phe Arg
65                  70                  75                  80

Gly Ser Ile Asn Ile Arg Asn Trp Leu Thr Asn Leu Asp Phe Gly Gln
                85                  90                  95

Glu Asp Cys Ser Leu Val Ser Gly Cys Gly Val His Ser Gly Phe Gln
            100                 105                 110

Arg Ala Trp Asn Glu Ile Ser Ser Gln Ala Thr Ala Ala Val Ala Ser
        115                 120                 125

Ala Arg Lys Ala Asn Pro Ser Phe Asn Val Ile Ser Thr Gly His Ser
    130                 135                 140

Leu Gly Gly Ala Val Ala Val Leu Ala Ala Ala Asn Leu Arg Val Gly
145                 150                 155                 160

Gly Thr Pro Val Asp Ile Tyr Thr Tyr Gly Ser Pro Arg Val Gly Asn
                165                 170                 175

Ala Gln Leu Ser Ala Phe Val Ser Asn Gln Ala Gly Gly Glu Tyr Arg
            180                 185                 190

Val Thr His Ala Asp Asp Pro Val Pro Arg Leu Pro Pro Leu Ile Phe
        195                 200                 205

Gly Tyr Arg His Thr Thr Pro Glu Phe Trp Leu Ser Gly Gly Gly Gly
    210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
                245                 250                 255

His Leu His Tyr Phe Gln Ala Thr Asp Ala Cys Asn Ala Gly Gly Phe
            260                 265                 270

Ser Trp Arg Arg
        275
```

<210> SEQ ID NO 10
<211> LENGTH: 273
<212> TYPE: PRT
<213> ORGANISM: Fusarium heterosporum

<400> SEQUENCE: 10

```
Thr Val Thr Thr Gln Asp Leu Ser Asn Phe Arg Phe Tyr Leu Gln His
1               5                   10                  15

Ala Asp Ala Ala Tyr Cys Asn Phe Asn Thr Ala Val Gly Lys Pro Val
            20                  25                  30

His Cys Ser Ala Gly Asn Cys Pro Asp Ile Glu Lys Asp Ala Ala Ile
        35                  40                  45
```

-continued

Val Val Gly Ser Val Val Gly Thr Lys Thr Gly Ile Gly Ala Tyr Val
    50                  55                  60

Ala Thr Asp Asn Ala Arg Lys Glu Ile Val Val Ser Val Arg Gly Ser
 65                  70                  75                  80

Ile Asn Val Arg Asn Trp Ile Thr Asn Phe Asn Phe Gly Gln Lys Thr
                    85                  90                  95

Cys Asp Leu Val Ala Gly Cys Gly Val His Thr Gly Phe Leu Asp Ala
                100                 105                 110

Trp Glu Glu Val Ala Ala Asn Val Lys Ala Val Ser Ala Ala Lys
                115                 120                 125

Thr Ala Asn Pro Thr Phe Lys Phe Val Val Thr Gly His Ser Leu Gly
    130                 135                 140

Gly Ala Val Ala Thr Ile Ala Ala Ala Tyr Leu Arg Lys Asp Gly Phe
145                 150                 155                 160

Pro Phe Asp Leu Tyr Thr Tyr Gly Ser Pro Arg Val Gly Asn Asp Phe
                165                 170                 175

Phe Ala Asn Phe Val Thr Gln Gln Thr Gly Ala Glu Tyr Arg Val Thr
                180                 185                 190

His Gly Asp Asp Pro Val Pro Arg Leu Pro Pro Ile Val Phe Gly Tyr
                195                 200                 205

Arg His Thr Ser Pro Glu Tyr Trp Leu Asn Gly Gly Pro Leu Asp Lys
    210                 215                 220

Asp Tyr Thr Val Thr Glu Ile Lys Val Cys Glu Gly Ile Ala Asn Val
225                 230                 235                 240

Met Cys Asn Gly Gly Thr Ile Gly Leu Asp Ile Leu Ala His Ile Thr
                245                 250                 255

Tyr Phe Gln Ser Met Ala Thr Cys Ala Pro Ile Ala Ile Pro Trp Lys
                260                 265                 270

Arg

<210> SEQ ID NO 11
<211> LENGTH: 278
<212> TYPE: PRT
<213> ORGANISM: Aspergillus oryzae

<400> SEQUENCE: 11

Asp Ile Pro Thr Thr Gln Leu Glu Asp Phe Lys Phe Trp Val Gln Tyr
 1                   5                  10                  15

Ala Ala Ala Thr Tyr Cys Pro Asn Asn Tyr Val Ala Lys Asp Gly Glu
                20                  25                  30

Lys Leu Asn Cys Ser Val Gly Asn Cys Pro Asp Val Glu Ala Ala Gly
            35                  40                  45

Ser Thr Val Lys Leu Ser Phe Ser Asp Asp Thr Ile Thr Asp Thr Ala
    50                  55                  60

Gly Phe Val Ala Val Asp Asn Thr Asn Lys Ala Ile Val Val Ala Phe
 65                  70                  75                  80

Arg Gly Ser Tyr Ser Ile Arg Asn Trp Val Thr Asp Ala Thr Phe Pro
                85                  90                  95

Gln Thr Asp Pro Gly Leu Cys Asp Gly Cys Lys Ala Glu Leu Gly Phe
                100                 105                 110

Trp Thr Ala Trp Lys Val Arg Asp Arg Ile Ile Lys Thr Leu Asp
            115                 120                 125

Glu Leu Lys Pro Glu His Ser Asp Tyr Lys Ile Val Val Val Gly His
    130                 135                 140

Ser Leu Gly Ala Ala Ile Ala Ser Leu Ala Ala Ala Asp Leu Arg Thr

```
               145                 150                 155                 160
Lys Asn Tyr Asp Ala Ile Leu Tyr Ala Tyr Ala Ala Pro Arg Val Ala
                165                 170                 175

Asn Lys Pro Leu Ala Glu Phe Ile Thr Asn Gln Gly Asn Asn Tyr Arg
                180                 185                 190

Phe Thr His Asn Asp Asp Pro Val Pro Lys Leu Pro Leu Leu Thr Met
                195                 200                 205

Gly Tyr Val His Ile Ser Pro Glu Tyr Tyr Ile Thr Ala Pro Asp Asn
                210                 215                 220

Thr Thr Val Thr Asp Asn Gln Val Thr Val Leu Asp Gly Tyr Val Asn
225                 230                 235                 240

Phe Lys Gly Asn Thr Gly Thr Ser Gly Gly Leu Pro Asp Leu Leu Ala
                245                 250                 255

Phe His Ser His Val Trp Tyr Phe Ile His Ala Asp Ala Cys Lys Gly
                260                 265                 270

Pro Gly Leu Pro Leu Arg
                275

<210> SEQ ID NO 12
<211> LENGTH: 278
<212> TYPE: PRT
<213> ORGANISM: Penicillium camemberti

<400> SEQUENCE: 12

Asp Val Ser Thr Ser Glu Leu Asp Gln Phe Glu Phe Trp Val Gln Tyr
1               5                   10                  15

Ala Ala Ala Ser Tyr Tyr Glu Ala Asp Tyr Thr Ala Gln Val Gly Asp
                20                  25                  30

Lys Leu Ser Cys Ser Lys Gly Asn Cys Pro Glu Val Glu Ala Thr Gly
                35                  40                  45

Ala Thr Val Ser Tyr Asp Phe Ser Asp Ser Thr Ile Thr Asp Thr Ala
                50                  55                  60

Gly Tyr Ile Ala Val Asp His Thr Asn Ser Ala Val Val Leu Ala Phe
65                  70                  75                  80

Arg Gly Ser Tyr Ser Val Arg Asn Trp Val Ala Asp Ala Thr Phe Val
                85                  90                  95

His Thr Asn Pro Gly Leu Cys Asp Gly Cys Leu Ala Glu Leu Gly Phe
                100                 105                 110

Trp Ser Ser Trp Lys Leu Val Arg Asp Asp Ile Ile Lys Glu Leu Lys
                115                 120                 125

Glu Val Val Ala Gln Asn Pro Asn Tyr Glu Leu Val Val Val Gly His
                130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175

Gly Asn Ala Ala Leu Ala Lys Tyr Ile Thr Ala Gln Gly Asn Asn Phe
                180                 185                 190

Arg Phe Thr His Thr Asn Asp Pro Val Pro Lys Leu Pro Leu Leu Ser
                195                 200                 205

Met Gly Tyr Val His Val Ser Pro Glu Tyr Trp Ile Thr Ser Pro Asn
                210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
```

```
                    245                 250                 255
Glu Ala His Ile Trp Tyr Phe Val Gln Val Asp Ala Gly Lys Gly Pro
                260                 265                 270

Gly Leu Pro Phe Lys Arg
        275

<210> SEQ ID NO 13
<211> LENGTH: 270
<212> TYPE: PRT
<213> ORGANISM: Aspergillus foetidus

<400> SEQUENCE: 13

Ser Val Ser Thr Ser Thr Leu Asp Glu Leu Gln Leu Phe Ala Gln Trp
1               5                   10                  15

Ser Ala Ala Ala Tyr Cys Ser Asn Asn Ile Asp Ser Lys Asp Ser Asn
                20                  25                  30

Leu Thr Cys Thr Ala Asn Ala Cys Pro Ser Val Glu Glu Ala Ser Thr
            35                  40                  45

Thr Met Leu Leu Glu Phe Asp Leu Thr Asn Asp Phe Gly Gly Thr Ala
        50                  55                  60

Gly Phe Leu Ala Ala Asp Asn Thr Asn Lys Arg Leu Val Val Ala Phe
65                  70                  75                  80

Arg Gly Ser Ser Thr Ile Glu Asn Trp Ile Ala Asn Leu Asp Phe Ile
                85                  90                  95

Leu Glu Asp Asn Asp Asp Leu Cys Thr Gly Cys Lys Val His Thr Gly
            100                 105                 110

Phe Trp Lys Ala Trp Glu Ser Ala Ala Asp Glu Leu Thr Ser Lys Ile
        115                 120                 125

Lys Ser Ala Met Ser Thr Tyr Ser Gly Tyr Thr Leu Tyr Phe Thr Gly
130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                165                 170                 175

Gly Asn Tyr Ala Leu Ala Glu His Ile Thr Ser Gln Gly Ser Gly Ala
            180                 185                 190

Asn Phe Arg Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Leu
                245                 250                 255

Ala His Leu Trp Tyr Phe Phe Ala Ile Ser Glu Cys Leu Leu
            260                 265                 270

<210> SEQ ID NO 14
<211> LENGTH: 270
<212> TYPE: PRT
<213> ORGANISM: Aspergillus niger

<400> SEQUENCE: 14

Ser Val Ser Thr Ser Thr Leu Asp Glu Leu Gln Leu Phe Ser Gln Trp
1               5                   10                  15

Ser Ala Ala Ala Tyr Cys Ser Asn Asn Ile Asp Ser Asp Asp Ser Asn
                20                  25                  30
```

```
Val Thr Cys Thr Ala Asp Ala Cys Pro Ser Val Glu Glu Ala Ser Thr
        35                  40                  45

Lys Met Leu Leu Glu Phe Asp Leu Thr Asn Asn Phe Gly Gly Thr Ala
 50                  55                  60

Gly Phe Leu Ala Ala Asp Asn Thr Asn Lys Arg Leu Val Val Ala Phe
 65                  70                  75                  80

Arg Gly Ser Ser Thr Ile Lys Asn Trp Ile Ala Asp Leu Asp Phe Ile
                85                  90                  95

Leu Gln Asp Asn Asp Asp Leu Cys Thr Gly Cys Lys Val His Thr Gly
                100                 105                 110

Phe Trp Lys Ala Trp Glu Ala Ala Asp Asn Leu Thr Ser Lys Ile
                115                 120                 125

Lys Ser Ala Met Ser Thr Tyr Ser Gly Tyr Thr Leu Tyr Phe Thr Gly
 130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Val
                165                 170                 175

Gly Asn Tyr Ala Leu Ala Glu His Ile Thr Ser Gln Gly Ser Gly Ala
                180                 185                 190

Asn Phe Pro Val Thr His Leu Asn Asp Ile Val Pro Arg Val Pro Pro
                195                 200                 205

Met Asp Phe Gly Phe Ser Gln Pro Ser Pro Glu Tyr Trp Ile Thr Ser
 210                 215                 220

Gly Thr Gly Ala Ser Val Thr Ala Ser Asp Ile Glu Leu Ile Glu Gly
225                 230                 235                 240

Ile Asn Ser Thr Ala Gly Asn Ala Gly Glu Ala Thr Val Asp Val Leu
                245                 250                 255

Ala His Leu Trp Tyr Phe Phe Ala Ile Ser Glu Cys Leu Leu
                260                 265                 270

<210> SEQ ID NO 15
<211> LENGTH: 269
<212> TYPE: PRT
<213> ORGANISM: Aspergillus oryzae

<400> SEQUENCE: 15

Asp Val Ser Ser Leu Leu Asn Asn Leu Asp Leu Phe Ala Gln Tyr
 1               5                  10                  15

Ser Ala Ala Ala Tyr Cys Asp Glu Asn Leu Asn Ser Thr Gly Thr Lys
                20                  25                  30

Leu Thr Cys Ser Val Gly Asn Cys Pro Leu Val Glu Ala Ala Ser Thr
        35                  40                  45

Gln Ser Leu Asp Glu Phe Asn Glu Ser Ser Tyr Gly Asn Pro Ala
 50                  55                  60

Gly Tyr Leu Ala Ala Asp Glu Thr Asn Lys Leu Leu Val Leu Ser Phe
 65                  70                  75                  80

Arg Gly Ser Ala Asp Leu Ala Asn Trp Val Ala Asn Leu Asn Phe Gly
                85                  90                  95

Leu Glu Asp Ala Ser Asp Leu Cys Ser Gly Cys Glu Val His Ser Gly
                100                 105                 110

Phe Trp Lys Ala Trp Ser Glu Ile Ala Asp Thr Ile Thr Ser Lys Val
                115                 120                 125

Glu Ser Ala Leu Ser Asp His Ser Asp Tyr Ser Leu Val Leu Thr Gly
 130                 135                 140
```

His Ser Tyr Gly Ala Ala Leu Ala Ala Leu Ala Ala Thr Ala Leu Arg
145                 150                 155                 160

Asn Ser Gly His Ser Val Glu Leu Tyr Asn Tyr Gly Gln Pro Arg Leu
            165                 170                 175

Gly Asn Glu Ala Leu Ala Thr Tyr Ile Thr Asp Gln Asn Lys Gly Gly
        180                 185                 190

Asn Tyr Arg Val Thr His Thr Asn Asp Ile Val Pro Lys Leu Pro Pro
    195                 200                 205

Thr Leu Leu Gly Tyr His His Phe Ser Pro Glu Tyr Tyr Ile Ser Ser
210                 215                 220

Ala Asp Glu Ala Thr Val Thr Thr Thr Asp Val Thr Glu Val Thr Gly
225                 230                 235                 240

Ile Asp Ala Thr Gly Gly Asn Asp Gly Thr Asp Gly Thr Ser Ile Asp
                245                 250                 255

Ala His Arg Trp Tyr Phe Ile Tyr Ile Ser Glu Cys Ser
            260                 265

<210> SEQ ID NO 16
<211> LENGTH: 251
<212> TYPE: PRT
<213> ORGANISM: Landerina penisapora

<400> SEQUENCE: 16

Pro Gln Asp Ala Tyr Thr Ala Ser His Ala Asp Leu Val Lys Tyr Ala
1               5                   10                  15

Thr Tyr Ala Gly Leu Ala Tyr Gln Thr Thr Asp Ala Trp Pro Ala Ser
            20                  25                  30

Arg Thr Val Pro Lys Asp Thr Thr Leu Ile Ser Ser Phe Asp His Thr
        35                  40                  45

Leu Lys Gly Ser Ser Gly Tyr Ile Ala Phe Asn Glu Pro Cys Lys Glu
    50                  55                  60

Ile Ile Val Ala Tyr Arg Gly Thr Asp Ser Leu Ile Asp Trp Leu Thr
65                  70                  75                  80

Asn Leu Asn Phe Asp Lys Thr Ala Trp Pro Ala Asn Ile Ser Asn Ser
                85                  90                  95

Leu Val His Glu Gly Phe Leu Asn Ala Tyr Leu Val Ser Met Gln Gln
            100                 105                 110

Val Gln Glu Ala Val Asp Ser Leu Leu Ala Lys Cys Pro Asp Ala Thr
        115                 120                 125

Ile Ser Phe Thr Gly His Ser Leu Gly Gly Ala Leu Ala Cys Ile Ser
    130                 135                 140

Met Val Asp Thr Ala Gln Arg His Arg Gly Ile Lys Met Gln Met Phe
145                 150                 155                 160

Thr Tyr Gly Gln Pro Arg Thr Gly Asn Gln Ala Phe Ala Glu Tyr Val
            165                 170                 175

Glu Asn Leu Gly His Pro Val Phe Arg Val Tyr Arg His Asp Ile
        180                 185                 190

Val Pro Arg Met Pro Pro Met Asp Leu Gly Phe Gln His His Gly Gln
    195                 200                 205

Glu Val Trp Tyr Glu Gly Asp Glu Asn Ile Lys Phe Cys Lys Gly Glu
210                 215                 220

Gly Glu Asn Leu Thr Cys Glu Leu Gly Val Pro Phe Ser Glu Leu Asn
225                 230                 235                 240

Ala Lys Asp His Ser Glu Tyr Pro Gly Met His
            245                 250

```
<210> SEQ ID NO 17
<211> LENGTH: 12
<212> TYPE: PRT
<213> ORGANISM: Artificial
<220> FEATURE:
<223> OTHER INFORMATION: Sequence used for alignment

<400> SEQUENCE: 17

Ala Cys Met Ser His Thr Trp Gly Glu Arg Asn Leu
1               5                   10

<210> SEQ ID NO 18
<211> LENGTH: 14
<212> TYPE: PRT
<213> ORGANISM: Artificial
<220> FEATURE:
<223> OTHER INFORMATION: Sequence used for alignment

<400> SEQUENCE: 18

His Gly Trp Gly Glu Asp Ala Asn Leu Ala Met Asn Pro Ser
1               5                   10
```

LIPASE VARIANTS

CROSS-REFERENCE TO RELATED APPLICATIONS

This application is a 35 U.S.C. 371 national application of PCT/US2007/060841 filed Jan. 22, 2007, which claims priority or the benefit under 35 U.S.C. 119 of U.S. provisional application Nos. 60/761,109 and 60/854,891 filed Jan. 23, 2006 and Oct. 27, 2006, respectively, the contents of which are fully incorporated herein by reference.

FIELD OF THE INVENTION

The present invention relates to lipase variants.

BACKGROUND OF THE INVENTION

Lipases are useful, e.g., as detergent enzymes to remove lipid or fatty stains from clothes and other textiles, as additives to dough for bread and other baked products. Thus, a lipase derived from *Thermomyces lanuginosus* (synonym *Humicola latuginosa*, EP 258 068 and ER 305 216) is sold for detergent use under the trade name Lipolase® (product of Novo Nordisk A/S), WO 0060063 describes variants of the *T. lanuginosus* lipase with a particularly good first-wash performance in a detergent solution. WO 9704079, WO 9707202 and WO 0032758 also disclose variants of the *T. lanuginosus* lipase.

In some applications, it is of interest to minimize the formation of odor-generating short-chain fatty acids. Thus, it is known that laundry detergents with lipases may sometimes leave residual odors attached to cloth soiled with milk (EP 430315). WO 02062973 discloses lipase variants where the odor generation has been reduced by attaching a C-terminal extension.

SUMMARY OF THE INVENTION

The inventors have found that by introducing mutations in certain regions/positions of a lipase it is possible to improve the properties or characteristics of the lipase.

In a preferred embodiment, the present invention relates to lipases having improved properties for use in detergents. For example, the invention provides variants with reduced tendency to odor generation obtained by introducing mutations in one or more regions identified in the parent lipase. In another preferred embodiment, the present invention provides lipase variants which, as compared to the parent lipase, have reduced potential for odor generation without the attachment of a C-terminal extension.

In a further aspect the invention relates to a DNA sequence encoding the lipase variant of the invention, an expression vector harbouring said DNA sequence and a transformed host cell containing the DNA sequence or the expression vector.

In another aspect, the invention provides a method of producing the lipase variant of the present invention.

BRIEF DESCRIPTION OF THE FIGURES

FIG. 1 shows the alignment of lipases.

SEQUENCE LISTINGS

SEQ ID NO: 1 shows the DNA sequence encoding lipase from *Thermomyces lanoginosus*.

SEQ ID NO: 2 shows the amino acid sequence of a lipase from *Thermomyces lanoginosus*.

SEQ ID NO: 3 shows the amino acid sequence of a lipase from *Absidia reflexa*.

SEQ ID NO: 4 shows the amino acid sequence of a lipase from *Absidia corymbifera*.

SEQ ID NO: 5 shows the amino acid sequence of a lipase from *Rhizomucor miehei*.

SEQ ID NO: 6 shows the amino acid sequence of a lipase from *Rhizopus oryzae*.

SEQ ID NO: 7 shows the amino acid sequence of a lipase from *Aspergillus niger*.

SEQ ID NO: 8 shows the amino acid sequence of a lipase from *Aspergillus tubingensis*.

SEQ ID NO: 9 shows the amino acid sequence of a lipase from *Fusarium oxysporum*.

SEQ ID NO: 10 shows the amino acid sequence of a lipase from *Fusarium heterosporum*.

SEQ ID NO: 11 shows the amino acid sequence of a lipase from *Aspergillus oryzae*.

SEQ ID NO: 12 shows the amino acid sequence of a lipase from *Penicillium camemberti*.

SEQ ID NO: 13 shows the amino acid sequence of a lipase from *Aspergillus foetidus*.

SEQ ID NO: 14 shows the amino acid sequence of a lipase from *Aspergillus niger*.

SEQ ID NO: 15 shows the amino acid sequence of a lipase from *Aspergillus oryzae*.

SEQ ID NO: 16 shows the amino acid sequence of a lipase from *Landenna penisepora*.

DETAILED DESCRIPTION OF THE INVENTION

Parent Lipases

Any suitable parent lipase may be used. In a preferred embodiment, the parent lipase may be a fungal lipase. In another preferred embodiment, the parent lipase may be a lipase with an amino acid sequence having at least 60%, 60%, 70%, 80%, 85%, 90%, 95%, 96%, 97%, 98%, 99% or even 100% homology as defined in the section "Homology and alignment" to the sequence of the *T. lanuginosus* lipase shown in SEQ ID NO: 2.

The parent lipase may be a yeast polypeptide such as a *Candida*, *Kluyveromyces*, *Pichia*, *Saccharomyces*, *Schizosaccharomyces*, or *Yarrowia* polypeptide; or more preferably a filamentous fungal polypeptide such as an *Acremonium*, *Aspergillus*, *Aureobasidium*, *Cryptococcus*, *Filobasidium*, *Fusarium*, *Humicole*, *Magnaporthe*, *Mucor*, *Myceliophthora*, *Neocallimastix*, *Neurospora*, *Paecilomyces*, *Penicillium*, *Piromyces*, *Schizophyllum*, *Talaromyces*, *Thermoascus*, *Thielavia*, *Tolypocladium*, or *Trichoderma* polypeptide.

In a preferred aspect, the parent lipase is a *Saccharomyces carlsbergensis*, *Saccharomyces cerevisiae*, *Saccharomyces diastaticus*, *Saccharomyces douglasli*, *Saccharomyces kluyveri*, *Saccharomyces norbensis*, or *Saccharomyces oviformis* polypeptide having lipase activity.

In another preferred aspect, the parent lipase is an *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Aspergillus turbigensis*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioldes*, *Fusarium venenatum*, *Humicola insolens*,

*Thermomyces lanoginosus* (synonym: *Humicola lanuginose*), *Mucor miehei, Myceliophthora thermophila, Neurospora crassa, Penicilliunm purpurogenum, Trichoderma harzianum, Trichoderma koningii, Trichoderma longibrachiatum, Trichoderma reesei,* or *Trichoderma viride* polypeptide.

In another preferred aspect, the parent lipase is a *Thermomyces lipase.*

In a more preferred aspect, the parent lipase is a *Thermomyces lanuginosus* lipase. In an even more preferred embodiment the parent lipase is the lipase of SEQ ID NO: 2.

Variant Lipases

The lipase variants of the present invention comprise, as compared to the parent lipase, at least three substitutions selected from the group consisting of:
 a) at least two substitution in Region I, and
 b) at least one substitution in Region II, and
 c) at least one substitution in Region III, and
 d) at least one substitution in Region IV;
 and wherein the variant has lipase activity.

In a preferred embodiment, the variant lipase is a variant of a *Thermomyces* lipase, more preferably, a *T. lanuginosus* lipase, and even more preferably, the *T. lanuginosus* lipase shown in SEQ ID NO, 2. In a preferred embodiment the variant lipase has at least 50%, 60%, 70%, 80%, 85%, 90%, 95%, 96%, 97%, 98% or 99% identity to SEQ ID NO:2.

The variant lipase may be a variant of a parent lipase encoded by a gene derived/obtained from one of the following parent organisms: *Candida, Kluyveromyces, Pichia, Saccharomyces, Schizosaccharomyces,* or *Yarrowia, Acremonium, Aspergillus, Aureobasidium, Cryptococcus, Filobasidium, Fusarium, Humicola, Magnaporthe, Mucor, Myceliophthore, Neocallimastix, Neurospora, Paecilomyces, Penicillium, Piromyces, Schizophyllum, Talaromyces, Thermoascus, Thielavia, Tolypocladium,* or *Trichoderma.* In a preferred embodiment, the variant lipase has at least 50%, 60%, 70%, 80%, 85%, 90%, 95%, 96%, 97%, 98% or 99% identity to a parent lipase encoded by a gene derived/obtained from one of the following parent organisms: *Candida, Kluyveromyces, Pichia, Saccharomyces, Schizosaccharomyces,* or *Yarrowia, Acremomium, Aspergillus, Aureobasidium, Cryptoccus, Filobasidium, Fusarum, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma.*

In a preferred aspect, the variant lipase is a variant *Saccharomyces carlsbergensis, Saccharomyces cerevisiae, Saccharomyces diastaticus, Saccharomyces douglasii, Saccharomyces kluyveri, Saccharomyces norbensis,* or *Sacrharomyces oviformis.* In a preferred embodiment, the variant lipase has at least 50%, 60%, 70%, 80%, 85%, 90%, 95%, 96%, 97%, 98% or 99% identity to a parent lipase encoded by a gene derived/ obtained from *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis.*

The variant lipase may be a variant of a parent lipase encoded by a gene derived/obtained from one of the following parent organisms: *Aspergillus aculeatus, Aspergillus awamori, Aspergillus fumigatus, Aspergillus foetidus, Aspergillus japonicus. Aspergillus nidulans, Aspergillus niger, Aspergillus oryzae, Aspergillus turbigensis, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcchroum, Fusarium sporotrichioides, Fusarium sulphureum, Fusaflum torulosum, Fusarium trichothecioides, Fusariuim venenatum, Humicola insolens, Thermomyces lanoginosus* (synonym, *Humicola lanuginose*). *Mucor miehei, Myceliophthora thermophila, Neurospora crassa, Penicillium purpurogenum, Trichoderma harzianum, Trichoderma koningli, Trichoderma longibrachiatum, Trichoderma reesei,* or *Trichoderma viride.* In a preferred embodiment, the variant lipase has at least 50%, 60%, 70%, 80%, 85%, 90%, 95%, 96%, 97%, 98% or 99% identity to a parent lipase encoded by a gene derived/obtained from one of the following parent organisms: *Aspergillus aculeatus, Aspergillus awamori, Aspergillus fumigatus, Aspergillus foetidus, Aspergillus japonicus, Aspergillus nidulans, Aspergillus niger, Aspergillus oryzae, Aspergillus turbigensis, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reficulatum, Fusarium roseum, Fusarium sambucinum, Fusarium sarcoahroum, Fusarium sporotrichioides, Fusarium sulphureum, Fusarium torulosum, Fusarium trichothedloides, Fusarium venenatum, Humicola insolens, Thermomyces lanoginosus* (synonym: *Humicola lanuginose*), *Mucor miehei, Myceliophthora thermophila, Neurospora crassa, Penicillium purpurogenum, Trichoderma harzianum, Trichoderma koningil, Trichoderma longibrachiatum, Trichoderma reesei,* or *Trichoderma viride.*

In another preferred aspect, the variant is a variant of a *Thermomyces* lipase.

In a more preferred aspect, the parent lipase is a *Thermomyces lanuginosus* lipase. In an even more preferred embodiment the parent lipase is the lipase of SEQ ID NO: 2.

Identification of Regions and Substitutions

The positions referred to in Region I through Region IV below are the positions of the amino acid residues in SEQ ID NO:2. To find the corresponding (or homologous) positions in a different lipase, the procedure described in "Homology and alignment" is used.

Substitutions in Region I

Region I consists of amino acid residues surrounding the N-terminal residue E1. In this region, it is preferred to substitute an amino acid of the parent lipase with a more positive amino acid. The lipase variant may comprise at least two substitutions in Region I, such as three, four five or six substitutions in Region I.

Amino acid residues corresponding to the following positions are comprised by Region I: 1, 2 to 11 and 223-239. The following positions are of particular interest: 1, 4, 8, 11, 223, 227, 229, 231, 233, 234, 236.

In particular the following substitutions have been identified: X1N/*X4V, X227G, X231R and X2S33R.

In a preferred embodiment the variant lipase has at least 80%, 85%, 90%, 95%, 96%, 97%, 98%, 99% identity to SEQ ID NO:2

In a most preferred embodiment the variant lipase is a variant of the lipase having the amino acid sequence of SEQ ID NO: 2.

Substitutions in Region II

Region II consists of amino acid residues in contact with substrate on one side of the acyl chain and one side of the alcohol part. In this region it is preferred to substitute an amino acid of the parent lipase with a more positive amino acid or with a less hydrophobic amino acid.

The lipase variant may comprise at least one substitution in Region II, such as two, three, four, five or six substitutions in Region I.

Amino acid residues corresponding to the following positions are comprised by Region II: 202 to 211 and 249 to 269. The following positions are of particular interest: 202, 210, 211, 253, 254, 255, 256.

In particular the following substitutions have been identified: X202G, X210K/W/A, X255Y/V/A and X256K/R and X259G/M/Q/V.

In a preferred embodiment the variant lipase has at least 80%, 85%, 90%, 95%, 96%, 97%) 98% or 99% identity to SEQ ID NO:2

In a most preferred embodiment the variant lipase is a variant of the lipase having the amino acid sequence of SEQ ID NO: 2.

Substitutions in Region III

Region III consists of amino acid residues that forms a flexible structure and thus allowing the substrate to got into the active site. In this region it is preferred to substitute an amino acid of the parent lipase with a more positive amino acid or a less hydrophobic amino acid.

The lipase variant may comprise at least one substitution in Region III, such as two, three, four, five or six substitutions in Region III.

Amino acid residues corresponding to the following positions are comprised by Region III: 82 to 102. The following positions are of particular interest: 83, 86, 87, 90, 91, 95, 96, 99.

In particular the following substitutions have been identified: X83T, X86V and X90A/R.

In a preferred embodiment the variant lipase has at least 80%, 85%, 90%, 95%, 96%, 97%, 98% or 99% identity to SEQ ID NO:2.

In a most preferred embodiment the variant lipase is a variant of the lipase having the amino acid sequence of SEQ ID NO: 2.

Substitutions in Region IV

Region IV consists of amino acid residues that binds electrostatically to a surface. In this region it is preferred to substitute an amino acid of the parent lipase with a more positive amino acid.

The lipase variant may comprise at least one substitution in Region IV, such as two, three, four, five or six substitutions in Region IV.

Amino acid residues corresponding to the following positions are comprised by Region IV: 27 and 54 to 62. The following positions are of particular interest: 27, 56, 57, 58, 60.

In particular the following substitutions have been identified: X27R, X58N/AG/T/P and X60V/S/G/N/R/K/A/L.

In a preferred embodiment the variant lipase has at least 80%, 85%, 90%, 95%, 96%, 97%, 98% or 99% identity to SEQ ID NO:2

In a most preferred embodiment the variant lipase is a variant of the lipase having the amino acid sequence of SEQ ID NO: 2.

Amino Acids at Other Positions

The parent lipase may optionally comprise additional alterations, e.g., substitution of other amino acids, particularly less than 10, less than 9, less than 8, less than 7, less than 6, less than 5 alterations as compared to a parent lipase. Examples are substitutions corresponding to one or more of the positions 24, 37, 38, 46, 74, 81, 83, 115, 127, 131, 137, 143, 147, 150, 199, 200, 203, 206, 211, 263, 284, 265, 267 and 269 of the parent lipase, In a particular embodiment there is a substitution in at least one of the positions corresponding to position 81, 147, 150, 227 and 249. In a preferred embodiment the at least one substitution is selected from the group consisting of X38R, X81Q/E, X143S/C/N/D/A, X147M/Y, X150G/K, X227G and X249R/I/L.

The variant may comprise substitutions outside the defined Region I to IV, the number of substitutions outside the defined Region I to IV is preferably less than six, such as five, four, three, two or one substitution.

Further substitutions may, e.g., be made according to principles known in the art, e.g. substitutions described in WO 92/05249, WO 94/25577, WO 95/22815, WO 97/04079 and WO 97/07202.

Parent Lipase Variants

Variant lipases include parent lipases having the substitutions listed below in table 1 (using SEQ ID NO:2 for numbering)

TABLE 1

| Region I | Region II | Region III | Region IV | Outside regions |
|---|---|---|---|---|
| X4V + X227G + X231R + X233R | X210K + X256K | X83T + X86V | X58A + X60S | X150G |
| X227G + X231R + X233R | X256K | X86V | X58N + X60S | X150G |
| X231R + X233R | X255Y | | | |
| X231R + X233R | X202G | | | |
| X227G + X231R + X233R | X256K | X86V | | |
| X4V + X231R + X233R | | | X58N + X60S | |
| X231R + X233R | | X90R | X58N + X60S | |
| X231R + X233R | X255V | X90A | | |
| X227G + X231R + X233R | X256K | X86V | X58N + X60S | X150G |
| X231R + X233R | X211L | | X58N + X60S | X147M |
| X231R + X233R | | | | X150K |

In a further particular embodiment, the parent lipase is identical to SEQ ID NO:2 and the variants of Table 1 will thus be:

TABLE 2

Some particular variants of SEQ ID NO: 2

| Region I | Region II | Region III | Region IV | Outside regions |
|---|---|---|---|---|
| Q4V + L227G + T231R + N233R | E210K + P256K | S83T + I86V | S58A + V60S | A150G |
| L227G + T231R + N233R | P256K | I86V | S58N + V60S | A150G |
| T231R + N233R | I255Y | | | |
| T231R + N233R | I202G | | | |
| L227G + T231R + N233R | P256K | I86V | | |
| Q4V + T231R + N233R | | | S58N + V60S | |
| T231R + N233R | | I90R | S58N + V60S | |
| T231R + N233R | I255V | I90A | | |
| L227G + T231R + N233R | P256K | I86V | S58N + V60S | A150G |
| T231R + N233R | F211L | | S58N + V60S | L147M |
| T231R + N233R | | | | A150K |

Nomenclature for Amino Acid Modifications

In describing lipase variants according to the invention, the following nomenclature is used for ease of reference:

Original amino acid(s):position(s):substituted amino acid(s)

According to this nomenclature, for instance the substitution of glutamic acid for glycine in position 195 is shown as G195E. A deletion of glycine in the same position is shown as G195*, and insertion of an additional amino acid residue such as lysine is shown as G195GK.

Where a specific lipase contains a "deletion" in comparison with other lipases and an insertion is made in such a position this is indicated as *36D for insertion of an aspartic acid in position 36.

Multiple mutations are separated by pluses, i.e., R170Y+ G195E, representing mutations in positions 170 and 195 substituting tyrosine and glutamic acid for arginine and glycine, respectively.

X231 indicates the amino acid in a parent polypeptide corresponding to position 231, when applying the described alignment procedure. X231R indicates that the amino acid is replaced with R. For SEQ ID NO:2 X is T, and X231R thus indicates a substitution of T in position 231 with R. Where the amino acid in a position (e.g. 231) may be substituted by another amino acid selected from a group of amino acids, e.g. the group consisting of R and P and Y, this will be indicated by X231R/P/Y.

In all cases, the accepted IUPAC single letter or triple letter amino acid abbreviation is employed.

Amino Acid Grouping

In this specification, amino acids are classified as negatively charged, positively charged or electrically neutral according to their electric charge at pH 10. Thus, negative amino acids are E, D, C (cysteine) and Y, particularly E and D. Positive amino acids are R, K and H, particularly R and K. Neutral amino acids are G, A, V, L, I, P, F W, S, T, M, N, Q and C when forming part of a disulfide bridge. A substitution with another amino acid in the same group (negative, positive or neutral) is termed a conservative substitution.

The neutral amino acids may be divided into hydrophobic or non-polar (G, A, V, L, I, P, F, W and C as part of a disulfide bridge) and hydrophilic or polar (S, T, M, N, Q).

Amino Acid Identity

The relatedness between two amino acid sequences or between two nucleotide sequences is described by the parameter "identity".

For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence", e.g. amino acids 1 to 269 of SEQ ID NO:2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap. The length of a sequence is the number of amino acid residues in the sequence (e.g. the length of SEQ ID NO:2 is 269).

The above procedure may be used for calculation of identity as well as homology and for alignment. In the context of the present invention homology and alignment has been calculated as described below.

Homology and Alignment

For purposes of the present invention, the degree of homology may be suitably determined by means of computer programs known in the art, such as GAP provided in the GCG program package (Program Manual for the Wisconsin Package, Version 8, August 1994% Genetics Computer Group, 575 Science Drive, Madison, Wis., USA 53711) (Needleman, S. B. and Wunsch, C. D, (1970), Journal of Molecular Biology. 48% 443-45), using GAP with the following settings for polypeptide sequence comparison: GAP creation penalty of 3.0 and GAP extension penalty of 0.1.

In the present invention, corresponding (or homologous) positions in the lipase sequences of *Absidia reflexa, Absidie corymbefera, Rhizmucor miehei, Rhizopus delemar Aspergillus niger, Aspergillus tubigensis, Fusarium oxysporum, Fusarium heterosporum, Aspergillus orzyea, Penicilium camembertii, Aspergillus foetidus, Aspergillus niger, Thermomyces lanoginosus* (synonym: *Humicola lanuginose*) and *Landerina penisapora* are defined by the alignment shown in FIG. 1.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program, GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). The following settings are used for polypeptide sequence comparison: GAP creation penalty of 3.0 and GAP extension penalty of 0.1.

Hybridization

The present invention also relates to isolated polypeptides having lipase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 178 to 660 of SEQ ID NO. 1, (ii) the cDNA sequence contained in nucleotides 178 to 660 of SEQ ID NO: 1, (iii) a subsequence of (i) or (ii), or (iv) a complementary strand of (i), (ii), or (iii) (J. Sambrook, E. F. Fritsch, and T. Maniatus, 1989, Molecular Cloning, A Laboratory Manual, 2d edition, Cold Spring Harbor, N.Y.). A subsequence of SEQ ID NO: 1 contains at least 100 contiguous nucleotides or preferably at feast 200 contiguous nucleotides. Moreover, the subsequence may encode a polypeptide fragment which has lipase activity.

For long probes of at least 100 nucleotides in length, very low to very high stringency conditions are defined as prehybridization and hybridization at 42° C. in 5×SSPE, 0.3% SDS, 200 ug/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SOS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

DNA Sequence, Expression Vector, Host Cell, Production of Lipase

The invention provides a DNA sequence encoding the lipase of the invention, an expression vector harboring the DNA sequence, and a transformed host cell containing the DNA sequence or the expression vector These may be obtained by methods known in the art.

The invention also provides a method of producing the lipase by culturing the trans-formed host cell under conditions conducive for the production of the lipase and recovering the lipase from the resulting broth. The method may be practiced according to principles known in the art.

Lipase Activity

Lipase Activity on Tributyrin at Neutral pH (LU)

A substrate for lipase is prepared by emulsifying tributyrin (glycerin tributyrate) using gum Arabic as emulsifier. The hydrolysis of tributyrin at 30° C. at pH 7 or 9 is followed in a pH-stat titration experiment. One unit of lipase activity (1 LU) equals the amount of enzyme capable of releasing 1 micro mol butyric acid/min at pH 7.

Benefit Risk

The Benefit Risk factor describing the performance compared to the reduced risk for odor smell is defined as: $BR=RP_{avg}/R$, as described below, Uses Enzymes of the present invention may find industrial use, e.g. be included in detergent compositions for removing of fatty matter.

EXAMPLES

Chemicals used as buffers and substrates were commercial products of at least reagent grade.

| Media and Solutions | |
|---|---|
| Product | Tradename |
| LAS: | Surfac PS |
| Zeolite A | Wessalith P |

Other ingredients used are standard laboratory reagents.

Materials
Product Supplier
EMPA221 EMPA St. Gallen, Lerchfeldstrasse 5, CH-9014 St. Gallen, Switzerland

Example 1

Production of Enzyme

A plasmid containing the gene encoding the lipase is constructed and transformed into a suitable host cell using standard methods of the art.

Fermentation is carried out as a fed-batch fermentation using a constant medium temperature of 34° C. and a start volume of 1.2 liter. The initial pH of the medium is set to 6.5. Once the pH has increased to 7.0 this value is maintained through addition of 10% % H3PO4. The level of dissolved oxygen in the medium is controlled by varying the agitation rate and using a fixed aeration rate of 1.0 liter air per liter medium per minute. The feed addition rate is maintained at a constant level during the entire fed-batch phase.

The batch medium contains maltose syrup as carbon source, urea and yeast extract as nitrogen source and a mixture of trace metals and salts. The feed added continuously during the fed-batch phase contains maltose syrup as carbon source whereas yeast extract and urea is added in order to assure a sufficient supply of nitrogen.

Purification of the lipase may be done by use of standard methods known in the art, e.g. by filtering the fermentation supernatant and subsequent hydrophobic chromatography and ion exchange chromatography, e.g. as described in EP 0 851 913 EPs Example 3.

Example 2

AMSA

Automated Mechanical Stress Assay—for calculation of Relative Performance (RP)

The enzyme variants of the present application are tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plates, test solutions, textile and lid are vigorously shaken to bring the test solution in contact with the textile and apply mechanical Stress. For further description see WO 02/42740 especially the paragraph "Special method embodiments" at page 23-24. The containers, which contain the detergent test solution, consist of cylindrical holes (6 mm diameter, 10 mm depth) in a metal plate. The stained fabric (test material) lies on the top of the metal plate and is used as a lid and seal on the containers. Another metal plate lies on the top of the stained fabric to avoid any spillage from each container. The two metal plate together with the stained fabric are vibrated up and down at a frequency of 30 Hz with an amplitude of 2 mm.

The assay is conducted under the experimental conditions specified below,

TABLE 3

| | |
|---|---|
| Test solution | 0.5 g/l LAS |
| | 0.52 g/l Na2CO3 |
| | 1.07 g/l Zeolite A |
| | 0.52 g/l Na3Citrat |
| Test solution volume | 160 micro l |
| pH | As is (≈9.9) |
| Wash time | 20 minutes |
| Temperature | 30° C. |
| Water hardness | 15° dH |
| | Ratio of $Ca^{2+}/Mg^{2+}/NaHCO_3$:4:1:7.5 |
| Enzyme concentration in test solution | 0.125, 0.25, 0.50, 1.0 mg ep/l |
| Drying | Performance: After washing the textile pieces is immediately flushed in tap water and air-dried at 85 C in 5 min Odor: After washing the textile pieces is immediately flushed in tap water and dried at room temperature (20° C.) for 2 hours |
| Test material | Cream turmeric swatch as described below (EMPA221 used as cotton textile) |

Cream-turmeric swatches were prepared by mixing 5 g of turmeric (Santa Maria, Denmark) with 100 g cream (38% fat, Ada, Denmark) at 50° C., the mixture was left at this temperature for about 20 minutes and filtered (50° C.) to remove any undissolved particles. The mixture is cooled to 20° C.) woven cotton swatches, EMPA221, were immersed in the crm-turmeric mixture and afterwards allowed to dry at room temperature over night and frozen until use. The preparation of cream-turmeric swatches is disclosed in the patent application WO 2006/125437.

The performance of the enzyme variant is measured as the brightness of the colour of the textile samples washed with that specific enzyme variant. Brightness can also be expressed as the intensity of the light reflected from the textile sample when luminated with white light. When the textile is stained the intensity of the reflected light is lower, than that of a clean textile. Therefore the intensity of the reflected light can be used to measure wash performance of an enzyme variant.

Color measurements are made with a professional flatbed scanner (PFU DL2400pro), which is used to capture an image of the washed textile samples. The scans are made with a resolution of 200 dpi and with an output color depth of 24 bits. In order to get accurate results, the scanner is frequently calibrated with a Kodak reflective ITS target.

To extract a value for the light intensity from the scanned images, a special designed software application is used (Novozymes Color Vector Analyzer). The program retrieves the 24 bit pixel values from the image and converts them into values for reds green and blue (RGB). The intensity value (Int) is calculated by adding the ROB values together as vectors and then taking the length of the resulting vector:

$$Int=\sqrt{r^2+g^2+b^2}.$$

The wash performance (P) of the variants is calculated in accordance with the below formula:

$$P=Int(v)-Int(r)$$

where

Int(v) is the light intensity value of textile surface washed with enzyme, and

Int(r) is the light intensity value of textile surface washed without enzyme.

A relative performance score is given as the result of the AMSA wash in accordance with the definition:

Relative Performance scores (RP) are summing up the performances (P) of the tested enzyme variants against the reference enzyme:

$$RP=P(\text{test enzyme})/P(\text{reference enzyme}).$$

RPavg indicates the average relative performance compared to the reference enzyme at all four enzyme concentrations (0.125, 0.25, 0.5, 1.0 mg epi)

$$RPavg=avg(RP(0.125),RP(0.25)RP(0.5),RP(1.0))$$

A variant is considered to exhibit improved wash performance, if it performs better than the reference, In the context of the present invention the reference enzyme is the lipase of SEQ ID NO:2 with the substitutions T231R+N233R.

Example 3

GC

Gas Chromatograph—for Calculation of Risk Factor

The butyric acid release from the lipase washed swatches were measured by Solid Phase Micro Extraction Gas Chromatography (SPME-GC) using the following method. Four textile pieces (5 mm in diameter), washed in the specified solution in Table 3 containing 1 mg/l lipase, were transferred to a Gas Chromatograph (GC) vial. The samples were analysed on a Varian 3800 GC equipped with a Stabilwax-DA w/Integra-Guard column (3 on, 0.32 mm ID and 0.25 micro-m df) and a Carboxen POMS SPME fibre (75 micro-m). Each sample was preincubated for 10 min at 40° C. followed by 20 min sampling with the SPME fibre in the head-space over the textile pieces. The sample was subsequently injected onto the column (injector temperature—250° C.). Column flow=2 ml Helium/min. Column oven temperature gradient: 0 min=40° C., 2 min=40° C., 22 min=2400° C., 32 min 240° C. The butyric acid was detected by FID detection and the amount of butyric acid was calculated based on a butyric acid standard curve.

The Risk Performance Odour, R, of a lipase variant is the ratio between the amount of released butyric acid from the lipase variant washed swatch and the amount of released butyric acid from a swatch washed with the lipase of SEQ ID NO: 2 with the substitutions T2S31R+N23SR (reference enzyme), after both values have been corrected for the amount of released butyric acid from a non-lipase washed swatch. The risk (R) of the variants is calculated in accordance with the below formula:

Odour=measured in micro g buturic acid developed at 1 mg enzyme protein/l corrected for blank $$Alpha_{last\ enzyme}=Odour_{test\ enzyme}-Blank$$

$$Alpha_{reference\ enzyme}=Odour_{reference\ enzyme}-Blank$$

$$R=Alpha_{test\ enzyme}/Alpha_{reference\ enzyme}$$

A variant is considered to exhibit reduced odor compared to the reference, if the R factor is lower than 1.

Example 4

Activity (LU) Relative to Absorbance at 280 nm

The activity of a lipase relative to the absorbance at 280 nm is determined by the following assay:

LU/A280:

The activity of the lipase is determined as described above in the section Lipase activity. The absorbance of the lipase at 280 nm is measured (A280) and the ratio LU/A280 is calculated, The relative LU/A280 is calculated as the LU/A280 of the variant divided by the LU/A280 of a reference enzyme. In the context of the present invention the reference enzyme is the lipase of SEQ ID NO:2 with the substitutions T231R+N 233R.

Example 5

BR

Benefit Risk

The Benefit Risk factor describing the performance compared to the reduced risk for odour smell is thus defined as:

$$BR=RP_{avg}/R$$

A variant is considered to exhibit improved wash performance and reduced odor, if the BR factor is higher than 1, Applying the above methods the following results were obtained:

TABLE 4

| Variant | Mutations in SEQ ID NO: 2 | Average RP ($RP_{avg}$) | BR | LU/A280 |
|---|---|---|---|---|
| 1 | I202G + T231R + N233R | 0.84 | 1.41 | not determined |
| 2 | I86V + L227G + T231R + N233R + P256K | 1.08 | 1.52 | 1700 |
| 3 | Q4V + S58N + V60S + T231R + N233R | 0.87 | 1.73 | 1950 |
| 4 | S58N + V60S + I90R + T231R + N233R | 1.06 | 1.27 | 2250 |
| 5 | I255Y + T231R + N233R | 1.19 | 1.17 | 3600 |
| 6 | I90A + T231R + N233R + I255V | 1.13 | 1.14 | 2700 |
| Reference | T231R + N233R | 1.00 | 1.00 | 3650 |
| 7 | G91A + E99K + T231R + N233R + Q249R + 270H + 271T + 272P + 273S + 274S + 275G + 276R + 277G + 278G + 279H + 280R | 0.43 | not determined | 850 |
| 8 | G91A + E99K + T231R, N233R + Q249R + 270H + 271T + 272P + 273S + 274S + 275G + 276R + 277G + 278G | 0.13 | not determined | 500 |

The reference lipase and variants 7 and 8 in Table 4 are described in WO 2000/060063.

Example 6

BR

Benefit Risk

The Benefit Risk was measured for the variants listed in Table 5. The Benefit Risk factor was measured in the same way as described in Example 5 and it was found to be above 1 for all the listed variants.

TABLE 5

| Variant | Mutations in SEQ ID NO: 2 |
|---|---|
| Reference | T231R + N233R |
| 9 | L97V + T231R + N233R |
| 10 | A150G + T231R + N233R |
| 11 | I90R + T231R + N233R |
| 12 | I202V + T231R + N233R |
| 13 | L227G + T231R + N233R + P256K |
| 14 | I90A + T231R + N233R |
| 15 | T231R + N233R + I255P |
| 16 | I90V + I255V + T231R + N233R |
| 17 | F211L + L227G + T231R + N233R + I255L + P256K |
| 18 | S58N + V60S + T231R + N233R + Q249L |
| 19 | S58N + V60S + T231R + N233R + Q249I |
| 20 | A150G + L227G + T231R + N233R + P256K |
| 21 | K46L + S58N + V60S + T231R + N233R + Q249L + D254I |
| 22 | Q4L + E43T + K46I + S58N + V60S + T231R + N233R + Q249L + D254I |
| 23 | Q4L + S58N + V60S + T231R + N233R + Q249L + D254I |
| 24 | K46I + S58N + V60S + T231R + N233R + Q249L + D254L |
| 25 | K46L + S58N + V60S + K223I + T231R + N233R + D254I |
| 26 | E43T + K46I + S58N + V60S + T231R + N233R + Q249L + D254I |
| 27 | S58N + V60S + I86V + A150G + L227G + T231R + N233R + P256K |
| 28 | K24R + K46R + K74R + I86V + K98R + K127R + D137K + A150G + K223R + T231R + N233R |
| 29 | S58A + V60A + I86V + T231R + N233R |
| 30 | K24R + K46R + S58N + V60S + K74R + I86V + K98R + K127R + D137K + K223R + T231R + N233R |
| 31 | S58A + V60A + I86V + A150G + T231R + N233R |
| 32 | S58N + V60V + D62G + T231R + N233R |
| 33 | Q4V + S58N + V60S + I86V + T231R + N233R + Q249L |
| 34 | Q4V + S58N + V60S + I86V + A150G + T231R + N233R + I255V |
| 35 | Q4V + S58N + V60S + I90A + A150G + T231R + N233R + I255V |
| 36 | Y53A + S58N + V60S + T231R + N233R + P256L |
| 37 | I202L + T231R + N233R + I255A |
| 38 | S58A + V60S + I86V + A150G + L227G + T231R + N233R + P256K |
| 39 | D27R + S58N + V60S + I86V + A150G + L227G + T231R + N233R + P256K |
| 40 | V60K + I86V + A150G + L227G + T231R + N233R + P256K |

TABLE 5-continued

| Variant | Mutations in SEQ ID NO: 2 |
|---|---|
| 41 | Q4V + S58A + V60S + S83T + I86V + A150G + E210K + L227G + T231R + N233R + P256K |
| 42 | Q4V + V60K + S83T + I86V + A150G + L227G + T231R + N233R + P256K |
| 43 | D27R + V60K + I86V + A150G + L227G + T231R + N233R + P256K |
| 44 | Q4N + L6S + S58N + V60S + I86V + A150G + L227G + T231R + N233R + P256K |
| 45 | E1N + V60K + I86V + A150G + L227G + T231R + N233R + P256K |
| 46 | V60K + I86V + A150G + K223N + G225S + T231R + N233R + P256K |
| 47 | E210V + T231R + N233R + Q249R |
| 48 | S58N + V60S + E210V + T231R + N233R + Q249R |
| 49 | Q4V + V60K + I90R + T231R + N233R + I255V |
| 50 | Q4V + V60K + A150G + T231R + N233R |
| 51 | V60K + S83T + T231R + N233R |
| 52 | V60K + A150G + T231R + N233R + I255V |
| 53 | T231R + N233G + D234G |
| 54 | S58N + V60S + I86V + A150G + E210K + L227G + T231R + N233R + Q249R + P256K |
| 55 | S58N + V60S + I86V + A150G + E210K + L227G + T231R + N233R + I255A + P256K |
| 56 | S58N + V60S + I86V + A150G + G156R + E210K + L227G + T231R + N233R + I255A + P256K |
| 57 | S58T + V60K + I86V + N94K + A150G + E210V + L227G + T231R + N233R + P256K |
| 58 | S58T + V60K + I86V + D102A + A150G + L227G + T231R + N233R + P256K |
| 59 | S58T + V60K + I86V + D102A + A150G + E210V + L227G + T231R + N233R + P256K |
| 60 | S58T + V60K + S83T + I86V + N94K + A150G + E210V + L227G + T231R + N233R + P256K |
| 61 | S58A + V60S + I86V + T143S + A150G + L227G + T231R + N233R + P256K |
| 62 | G91S + D96V + D254R |
| 63 | V60L + G91M + T231W + Q249L |
| 64 | T37A + D96A + T231R + N233R + Q249G |
| 65 | E56G + E87D + T231R + N233R + D254A |
| 66 | E210K + T231R + N233R |
| 67 | D27H + E87Q + D96N + T231R + N233R + D254V |
| 68 | F181L + E210V + T231R + N233R |
| 69 | D27N + D96G + T231R + N233R |
| 70 | D96N + T231R + N233R |
| 71 | T231R + N233I + D234G |
| 72 | S58K + V60L + E210V + Q249R |
| 73 | S58H + V60L + E210V + Q249R |
| 74 | Q4V + F55V + I86V + T231R + N233R + I255V |
| 75 | Q4V + S58T + V60K + T199L + N200A + E210K + T231R + N233R + I255A + P256K |
| 76 | Q4V + D27N + V60K + T231R + N233R |
| 77 | I90F + I202P + T231R + N233R + I255L |
| 78 | S58N + V60S + D158N + T231R + N233R |
| 79 | S58N + V60S + S115K + T231R + N233R |
| 80 | S58N + V60S + L147M + A150G + F211L + T231R + N233R |
| 81 | V60K + A150G + T231R + N233R |
| 82 | I90V + L227G + T231R + N233R + P256K |
| 83 | T231R + N233R + I255S |
| 84 | I86G + T231R + N233R |
| 85 | V60K + I202V + E210K + T231R + N233R + I255A + P256K |
| 86 | I90G + I202L + T231R + N233R + I255S |
| 87 | S58G + V60G + T231R + N233R |

The reference lipase is described in WO 2000/060063.

The invention claimed is:

1. A variant of a parent lipase, wherein the variant comprises the following substitutions (using SEQ ID NO: 2 for numbering):
   a) at least the following substitutions in Region I: X4V+X227G+X231R+X233R;
   b) at least the following substitutions in Region II: X210K+X256K;
   c) at least the following substitutions in Region III: X83T+X86V;
   d) at least the following substitutions in Region IV: X58A+X60S; and
   further comprising the substitution X150G; and
   wherein the variant has lipase activity and is at least 90% identical to SEQ ID NO: 2.

2. The lipase variant of claim 1, wherein the variant is at least 95% identical to SEQ ID NO: 2.

3. The lipase variant of claim 1, wherein the variant is at least 97% identical to SEQ ID NO: 2.

4. The lipase variant of claim 1, wherein the variant is at least 98% identical to SEQ ID NO: 2.

5. The lipase variant of claim 1, wherein the variant is at least 99% identical to SEQ ID NO: 2.

6. The lipase variant of claim 1, wherein the parent lipase is the lipase having the amino acid sequence of SEQ ID NO: 2.

7. The lipase variant of claim 1, which is Q4V+S58A+V60S+S83T+I86V+A150G+E210K+L227G+T231R+N233R+P256K.

8. The lipase variant of claim 1, further comprising at least one substitution in Region II selected from the group consisting of substitutions in positions corresponding to the positions 202, 211 and 255, or a combination thereof.

9. The lipase variant of claim 1, further comprising a substitution selected from the group consisting of X202G, X211L, and X255Y/V, or a combination thereof.

10. The lipase variant of claim 1, further comprising a substitution in Region III in a position corresponding to position 90.

11. The lipase variant of claim 1, further comprising a substitution which is X90A/R.

12. The lipase variant of claim 1, further comprising at least one substitution in Region IV in a position correspond to position 27.

13. The lipase variant of claim 1, further comprising a substitution which is X27R.

14. The lipase variant of claim 1, further comprising at least one substitution selected from the group consisting of substitutions in positions corresponding to position 81, 147, 227 and 249, or a combination thereof.

15. The lipase variant of claim 1, further comprising at least one substitution selected from the group consisting of X81Q/E, X147M/Y and X249R/I/L, or a combination thereof.

16. A DNA sequence encoding the lipase variant of claim 1.

17. A transformed host cell containing the DNA sequence of claim 16.

18. A method of producing a lipase variant, which comprises
   (a) culturing the transformed host cell of claim 17 under conditions conducive for the production of the lipase variant; and
   (b) recovering the lipase variant from the resulting broth.

* * * * *